(12) United States Patent
Roy

(10) Patent No.: US 9,435,755 B2
(45) Date of Patent: Sep. 6, 2016

(54) SCALABLE AND TUNABLE NEUTRON DETECTION INSTRUMENT

(71) Applicant: Rhombus Holdings LLC, Mountain View, CA (US)

(72) Inventor: Anshuman Roy, Mountain View, CA (US)

(73) Assignee: RHOMBUS HOLDINGS LLC, Mountain View, CA (US)

(*) Notice: Subject to any disclaimer, the term of this patent is extended or adjusted under 35 U.S.C. 154(b) by 254 days.

(21) Appl. No.: 13/894,305

(22) Filed: May 14, 2013

(65) Prior Publication Data

US 2014/0079171 A1    Mar. 20, 2014

Related U.S. Application Data

(60) Provisional application No. 61/703,718, filed on Sep. 20, 2012.

(51) Int. Cl.
  *G01T 3/08* (2006.01)
  *G01N 23/222* (2006.01)
  *B82Y 15/00* (2011.01)

(52) U.S. Cl.
  CPC ............ *G01N 23/222* (2013.01); *G01T 3/08* (2013.01); *B82Y 15/00* (2013.01); *Y10S 977/734* (2013.01); *Y10S 977/742* (2013.01)

(58) Field of Classification Search
  CPC ........ G01T 1/28; G01T 1/1644; G01T 1/249
  USPC ......................................... 250/370.1, 390.08
  See application file for complete search history.

(56) References Cited

U.S. PATENT DOCUMENTS 5,098,640 A    3/1992  Gozani et al.
5,399,863 A *  3/1995  Carron et al. ........... 250/370.05
(Continued)

FOREIGN PATENT DOCUMENTS

JP    2010056396    3/2010
WO   2009115956    9/2009

OTHER PUBLICATIONS

Sultan Salahuddin, et al., "Development of Active Pixel Photodiode Sensors for Gamma Camera Application", Proceedings of the International Conference on Electrical Engineering and Informatics, Institut Teknologi Bandung, Inonesia, Jun. 17-19, 2007.
(Continued)

*Primary Examiner* — David J Makiya
*Assistant Examiner* — Kenneth J Malkowski

(57) ABSTRACT

A method for detecting particles is presented. The method comprises generating a reaction to a plurality of particles using a converter material, wherein the converter material is operable to interact with the plurality of particles, and wherein a subset of the plurality of particles comprises neutrons. Further, the method comprises converting a response to the reaction to a readable electrical signal using a sensor, wherein the sensor comprises an array of pixels. Also, the method comprises processing the readable electrical signal from the sensor to generate information for each pixel on the array of pixels and transmitting the information to a processing unit. Also, the method comprises executing a discrimination procedure using the information for distinguishing between instances of impingement of neutrons and non-neutron particles on the array of pixels. Further, the method comprises determining the radionuclide or non-radionuclide source of origin of the neutron and non-neutron particles.

23 Claims, 9 Drawing Sheets

(56) References Cited

U.S. PATENT DOCUMENTS

| | | | |
|---|---|---|---|
| 5,479,023 A | 12/1995 | Bartle | |
| 5,519,225 A | 5/1996 | Mohr et al. | |
| 5,940,460 A * | 8/1999 | Seidel et al. | 376/153 |
| 7,847,260 B2 * | 12/2010 | Inbar | 250/370.11 |
| 8,558,187 B1 * | 10/2013 | Seidler, II | 250/390.01 |
| 2006/0169905 A1 | 8/2006 | Wenstrand | |
| 2006/0185165 A1 * | 8/2006 | Vafi et al. | 29/854 |
| 2007/0001123 A1 * | 1/2007 | Andrews | G01T 1/361 250/394 |
| 2009/0140150 A1 * | 6/2009 | Ivan et al. | 250/361 R |
| 2009/0269244 A1 | 10/2009 | Cunningham et al. | |
| 2010/0155611 A1 | 6/2010 | Fullwood et al. | |
| 2011/0095194 A1 * | 4/2011 | Orava et al. | 250/370.05 |
| 2012/0298846 A1 * | 11/2012 | Nomura | C07D 209/86 250/216 |
| 2014/0077092 A1 * | 3/2014 | Kopp | 250/390.01 |

OTHER PUBLICATIONS

Bouchami, et al., "Estimate of the neutron fields in ATLAS based on ATLAS-MPX detectors data", 12th International Workshop on Radiation Imaging Detectors, Robinson College, Cambridge, U.K., Jul. 11-15, 2010. Retrieved Feb. 27, 2013 from http://iopscience.iop.org/1748-0221/6/01/C01042.

Bouchami, et al., Estimate of the neutron fields in ATLAS based on ATLAS-MPX detectors data, 12th International Workshop on Radiation Imaging Detectors, Jul. 11-15, 2010, Robinson College, Cambridge U.K., published Jan. 11, 2011, http://iopscience.iop.org.

Sultan Salahuddin, et al., Development of Active Pixel Photodiode Sensors for Gamma Camera Application, Proceedings of the International Conference on Electrical Engineering and Informatics, Institut Teknologi Bandung, Indonesia Jun. 17-19, 2007.

Rynes, et al., Abstract of Gamma-ray and neutron radiography as part of a pulsed fast neutron analysis inspection system, Nuclear Instruments and methods in Physics Research Section A, Feb. 1999, p. 859-899, vol. 422, SOA/NASA ADS Physics Abstract Service, http://adsabs.harvard.edu.

* cited by examiner

SCALABLE AND TUNABLE NEUTRON DETECTION INSTRUMENT

CROSS-REFERENCE TO RELATED APPLICATIONS

Related Applications

This application is a conversion of and claims priority to and the benefit of Provisional Patent Application No. 61/703,718, entitled "Scalable and Tunable Neutron Detection Instrument," having a filing Date of Sep. 20, 2012, which is herein incorporated by reference in its entirety.

The present application is related to U.S. patent application Ser. No. 13/894,272, filed May 14, 2013, entitled "TUNABLE DETECTION INSTRUMENT FOR SUB-ATOMIC PARTICLES," naming Anshuman Roy as inventor. That application is incorporated herein by reference in its entirety and for all purposes.

FIELD OF THE INVENTION

Embodiments according to the present invention generally relate to detecting neutron particles and more specifically to a device for detecting neutron particles.

BACKGROUND OF THE INVENTION

Neutrons are subatomic particles with no net electric charge. Neutrons and protons, another subatomic particle, together form the nucleus of all elements in the periodic table except hydrogen. Free neutrons are produced as a consequence of either nuclear fission, radioactive decay of elements or fusion. Special nuclear materials ("SNMs") such as plutonium that are used for making dirty bombs decay radioactively to produce neutrons. Detection of such neutrons is an effective way of tracking the source of SNMs. However, since neutrons do not carry any electric charge, their detection is problematic as compared to other charged subatomic particles. One method of neutron detection that has been successfully employed is to use materials that can capture incident neutrons and convert them into other easily detectable subatomic particles, such as alpha particles, tritons, gamma rays, etc.

Historically, high-pressure Helium-3 (He3) tubes have been the mainstay of neutron detection. Neutrons impinging on these tubes interact with He3 nuclei to produce triton and protium, both of which are energetically charged subatomic particles that migrate in the presence of a strong electric field inside the tubes towards the electrodes. Unfortunately, He3 supplies on the planet are running low and the price of He3 in recent years has increased twenty-fold in the last decade alone. Thus, there is a strong consensus in the field to replace He3 technology with alternatives, mostly scintillation based detection systems and Boron lined proportional tubes.

Scintillator detectors also have several limitations. First, scintillation crystals are expensive and made in small volumes due to a limited market. Second, complicated pulse shape discrimination algorithms need to be employed in these systems to discriminate neutrons from gamma rays, which also interact heavily with the scintillating crystals. Scintillation detectors also suffer from reliability issues on the field due to the use of scintillating crystals that can be sensitive to environmental factors such as humidity and salinity. The gamma discrimination capability of Boron lined tubes is better than scintillator detectors. However, being a proportional counter technology, Boron lined tubes are limited by their form factor in the scope of their applications. Moreover, there is an absence of a global supply chain to drive down their cost over time. Both scintillation and proportional counter based systems must contend with significant system-level noise that interferes with measurements of low incident neutron flux levels close to the cosmic background. They also lack modularity, flexibility to detect subatomic particles other than neutrons, and potential for rapid scalability.

BRIEF SUMMARY OF THE INVENTION

Accordingly, what is needed is a technology for neutron detection that employs readily available and easily replaceable components that are readily tunable to detect neutrons and designed to be modular. Further, the technology needs to be flexible so that other subatomic or other particles besides neutrons can also be detected.

Disclosed herein is a modular and tunable technology platform comprising simple, easy-to-acquire, off-the-shelf components that are modified and assembled together to form a highly sensitive, high-performance instrument. The off-the-shelf components used to assemble the device may be tuned to be sensitive to different particles including neutrons. The readily available and easily replaceable components of the present invention may be tuned to be sensitive to neutrons of different energies. The architecture of the embodiments of the invention disclosed herein not only allows for rapid, sensitive and flexible detection and imaging of neutrons, especially thermal neutrons, but also of a wide variety of other subatomic particles that may accompany neutrons that originate from an SNM source. The system architecture also enables identification of the element (radionuclide) that acts as a source of the incident neutrons. The architecture also enables tracking the direction of the source of neutrons and identification of the radionuclide or non-radionuclide source from which the neutrons originated. Finally, the architectures of the embodiments of the invention disclosed herein enable real time gamma discrimination thereby reducing false positives and response times of the instrument.

In one embodiment, a method for detecting particles is disclosed. The method comprises generating a reaction to a plurality of particles using a converter material, wherein the converter material is operable to interact with the plurality of particles, and wherein a subset of the plurality of particles comprises neutrons. Further, the method comprises converting a response to the reaction to a readable electrical signal using a sensor, wherein the sensor comprises an array of pixels. Also, the method comprises processing the readable electrical signal from the sensor to generate information for each pixel on the array of pixels and transmitting the information to a processing unit. Finally, the method comprises executing a discrimination procedure using the information for distinguishing between instances of impingement of neutrons and instances of impingement of non-neutron particles on the array of pixels.

In one embodiment, an apparatus for detecting neutrons is disclosed. The apparatus comprises a converter layer operable to interact with and generate a reaction to a plurality of particles, wherein a subset of the plurality of particles comprises neutrons. It also comprises a sensor coupled to the converter layer, wherein the sensor is operable to convert a response to the reaction to a readable electrical signal, and wherein the sensor comprises an array of discrete pixel sensors each with a respective (x,y) coordinate within the array. The apparatus further comprises a first processing device operable to process the readable electrical signal to generate information for each pixel on the array and a second processing device communicatively coupled to the first processing device. The second processing device is configured to: (a) control the first processing device; (b) receive the information from the first processing device; and (c) execute a discrimination procedure using the information to distinguish between instances of impingement of neutrons and instances of impingement of non-neutron particles on the array.

In one embodiment, a system for detecting neutrons is disclosed. The system comprises a plurality of sensor modules, wherein each sensor module comprises a plurality of sensor elements and a first processing device. Each of the sensor elements comprises at least one converter layer operable to interact with and generate a reaction to a plurality of particles, wherein a subset of the plurality of particles comprises neutrons. Each sensor element also comprises a sensor coupled to the at least one converter layer, wherein the sensor is operable to convert a response to the reaction to a readable electrical signal. Further, the sensor comprises an array of discrete pixel sensors each with a respective (x,y) coordinate within the array. The system can also comprise a second processing device communicatively coupled to the plurality of sensor modules, wherein the second processing device is operable to read information regarding a respective readable electrical signal from a respective first processing device on each of the plurality of sensor modules. Further, the second processing device is operable to execute a discrimination procedure using the information to distinguish between instances of impingement of neutrons and instances of impingement of non-neutron particles on respective arrays of pixel sensors associated with the plurality of sensor modules. Finally, the system comprises a housing to encapsulate the plurality of sensor modules, wherein at least one of the plurality of sensor modules is tuned to detect a neutron and at least one of the plurality of sensor modules is tuned to detect a non-neutron particle.

The following detailed description together with the accompanying drawings will provide a better understanding of the nature and advantages of the present invention.

BRIEF DESCRIPTION OF THE DRAWINGS

Embodiments of the present invention are illustrated by way of example, and not by way of limitation, in the figures of the accompanying drawings and in which like reference numerals refer to similar elements.

DETAILED DESCRIPTION OF THE INVENTION

Figure 1:
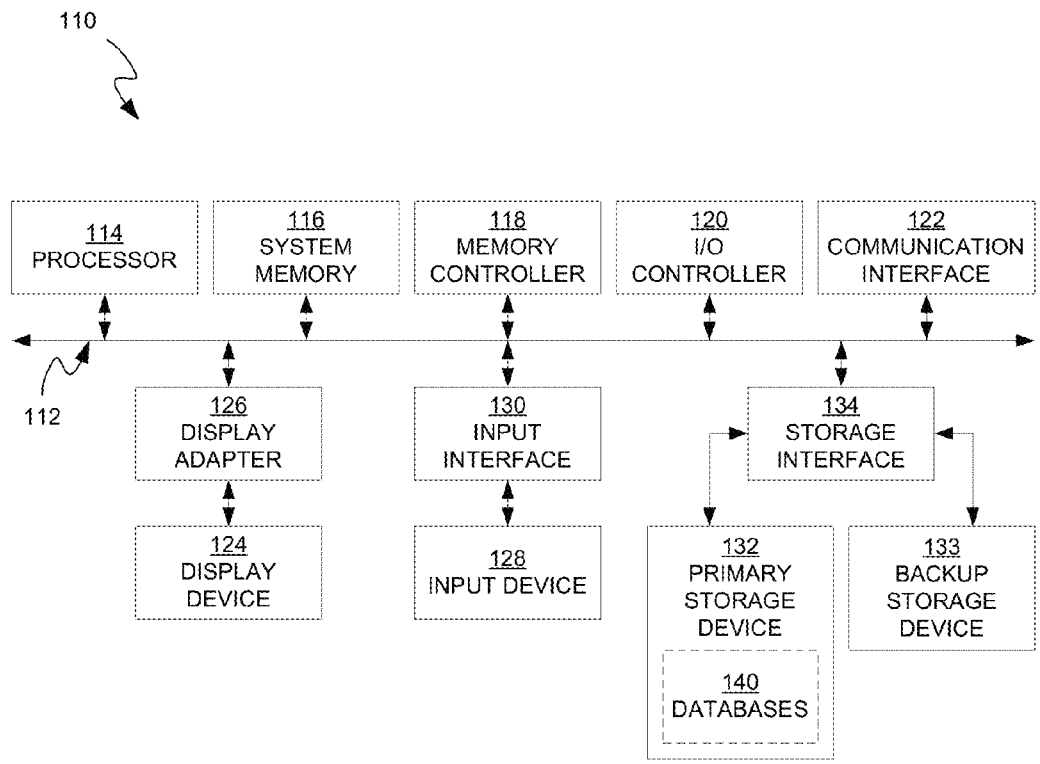
FIG. 1 is a block diagram of an example of a computing system capable of implementing embodiments of the present disclosure.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "generating," "converting," "processing," "analyzing," "transmitting," "allocating," "detecting," "associating," "accessing," "erasing," "freeing," "controlling," "determining," "identifying," or the like, refer to actions and processes (e.g., flowchart 800 of FIG. 8) of a computer system or similar electronic computing device or processor (e.g., system 110 of FIG. 1). The computer system or similar electronic computing device manipulates and transforms data represented as physical (electronic) quantities within the computer system memories, registers or other such information storage, transmission or display devices.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer-readable storage media and communication media; non-transitory computer-readable media include all computer-readable media except for a transitory, propagating signal. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared, and other wireless media. Combinations of any of the above can also be included within the scope of computer-readable media.

FIG. 1 is a block diagram of an example of a computing system for a neutron and other subatomic particles detecting system 110 capable of implementing embodiments of the present disclosure. Computing system 110 broadly represents any single or multi-processor computing device or system capable of executing computer-readable instructions. Examples of computing system 110 include, without limitation, workstations, laptops, client-side terminals, servers, distributed computing systems, handheld devices, or any other computing system or device. In its most basic configuration, computing system 110 may include at least one processor 114 and a system memory 116.

Processor 114 generally represents any type or form of processing unit capable of processing data or interpreting and executing instructions. In certain embodiments, processor 114 may receive instructions from a software application or module. These instructions may cause processor 114 to perform the functions of one or more of the example embodiments described and/or illustrated herein.

System memory 116 generally represents any type or form of volatile or non-volatile storage device or medium capable of storing data and/or other computer-readable instructions. Examples of system memory 116 include, without limitation, RAM, ROM, flash memory, or any other suitable memory device. Although not required, in certain embodiments computing system 110 may include both a volatile memory unit (such as, for example, system memory 116) and a non-volatile storage device (such as, for example, primary storage device 132).

Computing system 110 may also include one or more components or elements in addition to processor 114 and system memory 116. For example, in the embodiment of FIG. 1, computing system 110 includes a memory controller 118, an input/output (I/O) controller 120, and a communication interface 122, each of which may be interconnected via a communication infrastructure 112. Communication infrastructure 112 generally represents any type or form of infrastructure capable of facilitating communication between one or more components of a computing device. Examples of communication infrastructure 112 include, without limitation, a communication bus (such as an Industry Standard Architecture (ISA), Peripheral Component Interconnect (PCI), PCI Express (PCIe), or similar bus and a network.

Memory controller 118 generally represents any type or form of device capable of handling memory or data or controlling communication between one or more components of computing system 110. For example, memory controller 118 may control communication between processor 114, system memory 116, and I/O controller 120 via communication infrastructure 112.

I/O controller 120 generally represents any type or form of module capable of coordinating and/or controlling the input and output functions of a computing device. For example, I/O controller 120 may control or facilitate transfer of data between one or more elements of computing system 110, such as processor 114, system memory 116, communication interface 122, display adapter 126, input interface 130, and storage interface 134.

Communication interface 122 broadly represents any type or form of communication device or adapter capable of facilitating communication between example computing system 110 and one or more additional devices. For example, communication interface 122 may facilitate communication between computing system 110 and a private or public network including additional computing systems. Examples of communication interface 122 include, without limitation, a wired network interface (such as a network interface card), a wireless network interface (such as a wireless network interface card), a modem, and any other suitable interface. In one embodiment, communication interface 122 provides a direct connection to a remote server via a direct link to a network, such as the Internet. Communication interface 122 may also indirectly provide such a connection through any other suitable connection.

Communication interface 122 may also represent a host adapter configured to facilitate communication between computing system 110 and one or more additional network or storage devices via an external bus or communications channel. Examples of host adapters include, without limitation, Small Computer System Interface (SCSI) host adapters, Universal Serial Bus (USB) host adapters, IEEE (Institute of Electrical and Electronics Engineers) 1394 host adapters, Serial Advanced Technology Attachment (SATA) and External SATA (eSATA) host adapters, Advanced Technology Attachment (ATA) and Parallel ATA (PATA) host adapters, Fibre Channel interface adapters, Ethernet adapters, or the like. Communication interface 122 may also allow computing system 110 to engage in distributed or remote computing. For example, communication interface 122 may receive instructions from a remote device or send instructions to a remote device for execution.

As illustrated in FIG. 1, computing system 110 may also include at least one display device 124 coupled to communication infrastructure 112 via a display adapter 126. Display device 124 generally represents any type or form of device capable of visually displaying information forwarded by display adapter 126. Similarly, display adapter 126 generally represents any type or form of device configured to forward graphics, text, and other data for display on display device 124.

As illustrated in FIG. 1, computing system 110 may also include at least one input device 128 coupled to communication infrastructure 112 via an input interface 130. Input device 128 generally represents any type or form of input device capable of providing input, either computer- or human-generated, to computing system 110. Examples of input device 128 include, without limitation, a keyboard, a pointing device, a speech recognition device, or any other input device.

As illustrated in FIG. 1, computing system 110 may also include a primary storage device 132 and a backup storage device 133 coupled to communication infrastructure 112 via a storage interface 134. Storage devices 132 and 133 generally represent any type or form of storage device or medium capable of storing data and/or other computer-readable instructions. For example, storage devices 132 and 133 may be a magnetic disk drive (e.g., a so-called hard drive), a floppy disk drive, a magnetic tape drive, an optical disk drive, a flash drive, or the like. Storage interface 134 generally represents any type or form of interface or device for transferring data between storage devices 132 and 133 and other components of computing system 110.

In one example, databases 140 may be stored in primary storage device 132. Databases 140 may represent portions of a single database or computing device or it may represent multiple databases or computing devices. For example, databases 140 may represent (be stored on) a portion of computing system 110 and/or portions of example network architecture 200 in FIG. 2 (below). Alternatively, databases 140 may represent (be stored on) one or more physically separate devices capable of being accessed by a computing device, such as computing system 110 and/or portions of network architecture 200.

Continuing with reference to FIG. 1, storage devices 132 and 133 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 132 and 133 may also include other similar structures or devices for allowing computer software, data, or other computer-readable instructions to be loaded into computing system 110. For example, storage devices 132 and 133 may be configured to read and write software, data, or other computer-readable information. Storage devices 132 and 133 may also be a part of computing system 110 or may be separate devices accessed through other interface systems.

Many other devices or subsystems may be connected to computing system 110. Conversely, all of the components and devices illustrated in FIG. 1 need not be present to practice the embodiments described herein. The devices and subsystems referenced above may also be interconnected in different ways from that shown in FIG. 1. Computing system 110 may also employ any number of software, firmware, and/or hardware configurations. For example, the example embodiments disclosed herein may be encoded as a computer program (also referred to as computer software, software applications, computer-readable instructions, or computer control logic) on a computer-readable medium.

The computer-readable medium containing the computer program may be loaded into computing system 110. All or a portion of the computer program stored on the computer-readable medium may then be stored in system memory 116 and/or various portions of storage devices 132 and 133. When executed by processor 114, a computer program loaded into computing system 110 may cause processor 114 to perform and/or be a means for performing the functions of the example embodiments described and/or illustrated herein. Additionally or alternatively, the example embodiments described and/or illustrated herein may be implemented in firmware and/or hardware.

A computer program for controlling the particle detection system may be stored on the computer readable medium and then stored in system memory 116 and/or various portions of storage devices 132 and 133. When executed by the processor 114, the computer program may cause the processor 114 to perform and/or be a means for performing the functions required for carrying out particle detection.

Figure 2:
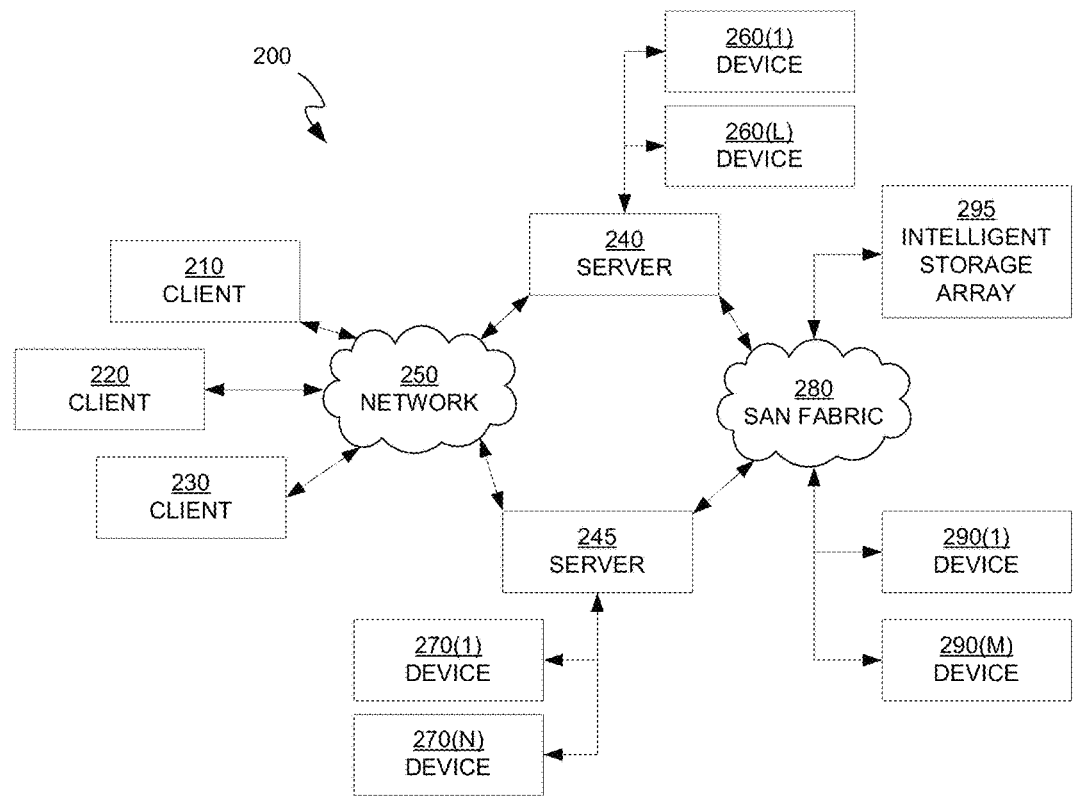
FIG. 2 is a block diagram of an example of a network architecture in which client systems and servers may be coupled to a network, according to embodiments of the present invention.

FIG. 2 is a block diagram of an example of a network architecture 200 in which client systems 210, 220, and 230 and servers 240 and 245 may be coupled to a network 250. Client systems 210, 220, and 230 generally represent any type or form of computing device or system, such as computing system 110 of FIG. 1.

Similarly, servers 240 and 245 generally represent computing devices or systems, such as application servers or database servers, configured to provide various database services and/or run certain software applications. Network 250 generally represents any telecommunication or computer network including, for example, an intranet, a wide area network (WAN), a local area network (LAN), a personal area network (PAN), or the Internet.

With reference to computing system 110 of FIG. 1, a communication interface, such as communication interface 122, may be used to provide connectivity between each client system 210, 220, and 230 and network 250. Client systems 210, 220, and 230 may be able to access information on server 240 or 245 using, for example, a Web browser or other client software. Such software may allow client systems 210, 220, and 230 to access data hosted by server 240, server 245, storage devices 260(1)-(L), storage devices 270(1)-(N), storage devices 290(1)-(M), or intelligent storage array 295. Although FIG. 2 depicts the use of a network (such as the Internet) for exchanging data, the embodiments described herein are not limited to the Internet or any particular network-based environment.

In one embodiment, all or a portion of one or more of the example embodiments disclosed herein are encoded as a computer program and loaded onto and executed by server 240, server 245, storage devices 260(1)-(L), storage devices 270(1)-(N), storage devices 290(1)-(M), intelligent storage array 295, or any combination thereof. All or a portion of one or more of the example embodiments disclosed herein may also be encoded as a computer program, stored in server 240, run by server 245, and distributed to client systems 210, 220, and 230 over network 250.

Scalable and Tunable Neutron Detection Instrument

Embodiments of the present invention provide methods and systems for detecting neutrons and other subatomic particles. While the discussion below predominantly focuses on subatomic particles including neutrons, embodiments and principles of the present invention can also be used to detect atomic species, e.g., ions, gases, etc. or molecular species as well.

Disclosed herein is a modular and tunable technology platform comprising readily available, easy-to-acquire, off-the-shelf components that are assembled together to form a highly sensitive, high-performance instrument. The off-the-shelf components used to assemble the device may be tuned to be sensitive to different particles. The architecture of the invention disclosed herein allows for rapid, sensitive and flexible detection and identification of a wide variety of subatomic particles such as neutrons, gamma rays, beta particles, alpha particles, neutrinos, muons, etc. using the same instrument. Also, the particle detection device of embodiments of the present invention can be designed using solid-state electronics which helps reduce noise and vibration.

Figure 3:
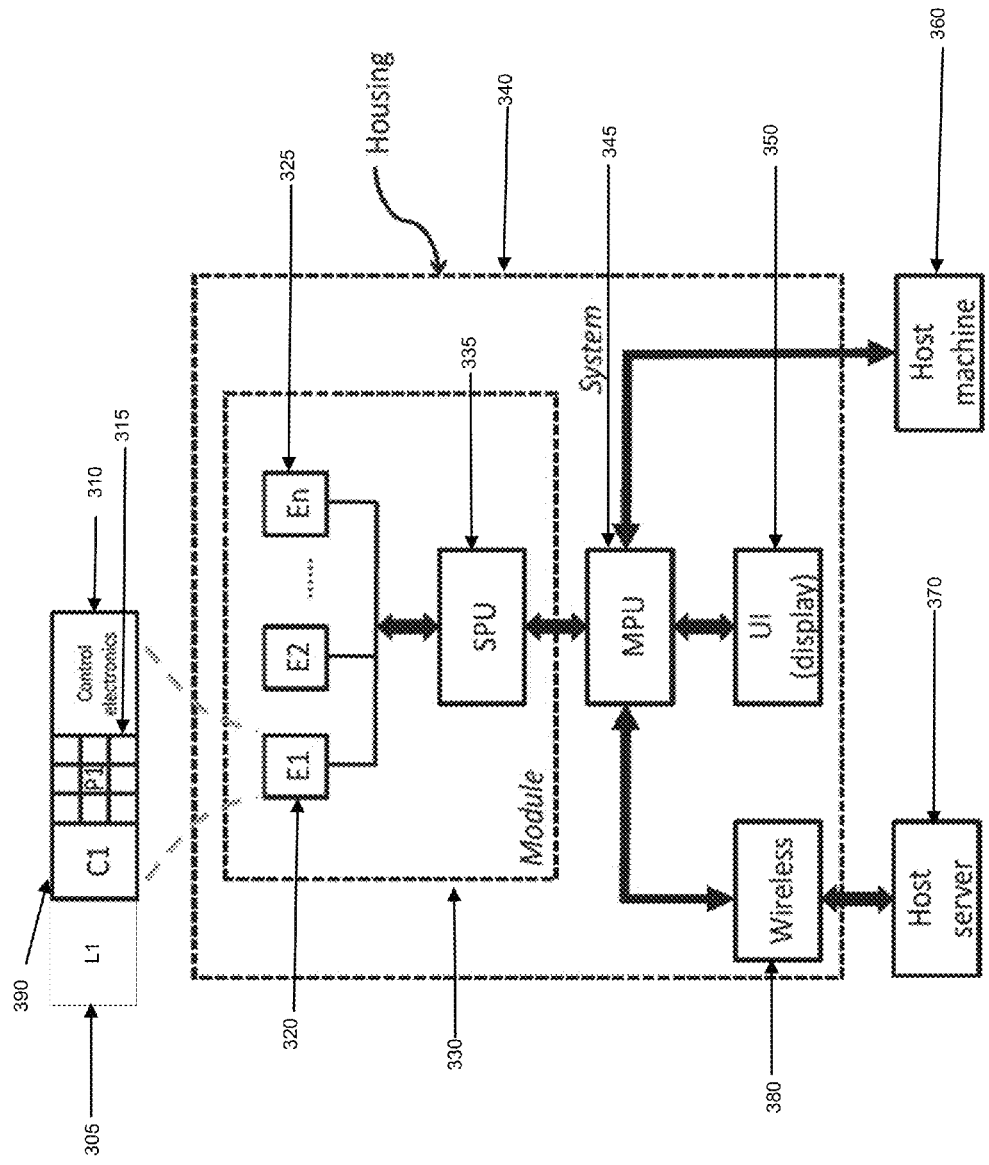
FIG. 3 is an exemplary block diagram of a subatomic particle detection system in accordance with one embodiment of the present invention.

FIG. 3 is an exemplary block diagram of a subatomic particle detection system in accordance with one embodiment of the present invention. The system can have a hierarchical architecture comprising elements and modules that are arranged in a configuration specific to the application. FIG. 3 illustrates a system comprising "N" number of elements, from element E1 320 to element En 325. These elements comprise the basic building blocks of the system. Each module 330 within the system may comprise hundreds or even thousands of elements. Accordingly, the number of elements "N" may only be bounded by practical considerations.

As shown in FIG. 3, in one embodiment, each element may have a converter layer, C1 390, that interacts with incident subatomic particles. In one embodiment, converter layer, C1 390, can be a thin film material that can be applied directly to the sensor. The design of the system is tunable because different materials (referred to herein interchangeably as "converter materials" or "reactive materials") can be used to develop C1 390 so as to make the elements sensitive to different subatomic particles.

For example, in one embodiment, the system may be tuned for neutron detection by making C1 a layer of reactive neutron-capturing materials such as $^{157}$Gadolinium (also known as "native Gadolinium" which is a mixture of several isotopes including $^{157}$Gadolinium), $^{10}$Boron (also known as native Boron), $^{6}$Lithium (also known as native Lithium), etc. These converter layers may be in pure elemental form or in compound form or be a mixture of elements and compounds of neutron absorbing isotopes of elements in any combination. In a different embodiment, the system may be tuned for gamma detection by developing C1 with a reactive material that interacts with gamma rays such as Cesium Iodide, Sodium Iodide, etc. In another embodiment, the system may be tuned for fast neutron detection by designing C1 with a layer of polyethylene, paraffin wax, any compound from the epoxy or silicone families, or other such hydrogenous material. In one embodiment, C1 can be designed to be placed in conjunction with a hydrogenous material as well. In another embodiment, one or more groups of elements may be coated with different converter layers.

In one embodiment, C1 can be selected from the following: Xenon, Cadmium, Hafnium, Gadolinium, Cobalt, Samarium, Lithium, Titanium, Europium, Molybdenum, Ytterbium, Dysprosium, Erbium, and Boron in their native form, or isotope enriched form, as well as compounds from the foregoing list in their native or isotope enriched forms, such as but not limited to oxides, carbides, halides (e.g., iodides, chlorides, to name a few), etc. as well as combinations of the elements in a blend/alloy form or compounds of such combinations, such as Gadolinium Titanate, Boron Carbide, DiMolybdenum Pentaboride ($Mo_2B_5$) etc.

The converter layers may be deposited by vapor state, liquid state or plasma state deposition techniques. In one manifestation, the converter layer used can be a fullerene compound of lithium, C60AxLix, that is deposited from solution state using a combination of solvents such as chlorobenzene and dichlorobenzene. In another embodiment, modified Boron fullerenes can be deposited from the solution state. In one embodiment, converter layer can also be nanotube or graphene compound (made of any material comprising a molecule from the carbon based fullerene family such as $C_{60}$, $C_{70}$, $C_{84}$ etc.) chemically attached or bonded to a neutron absorbing element or compound. The carbon based fullerene molecule in this case can be chemically bonded to a neutron absorbing molecule, either inside (endohedral fullerenes) or outside the fullerene cage. The fullerene molecule may also be made with Boron, such as Boron Fullerene, in which case there is no need for a carbon based fullerene molecule.

In one embodiment, each element may also comprise a sensor array of pixels, P1 315, that convert incoming particles, such as products of the interaction between the incident subatomic particles and C1 315, to an electrical output that may be converted from analog to a digital signal through a combination of transistors and analog to digital converters at the pixel level or separately. These transistors and analog to digital converters may reside in a control electronics module 310, wherein each element comprises its own control electronics module 310. In one embodiment, sensor array P1 315 may be an off-the-shelf sensor. The sensor, for example, among other things, could be a memristor or an image sensor or a photon detector or a photovoltaic cell. The sensor could also be a type of sensor commonly used in conventional consumer electronic device digital cameras.

In one embodiment, P1 315 is made from any material that can detect charged particles, some examples of which include semiconducting polymers, e.g., Poly(3-hexylthiphene), Poly[[9-(1-octylnonyl)-9H-carbazole-2,7-diyl]-2,5-thiophenediyl-2,1,3-benzothiadiazole-4,7-diyl-2,5-thio-phenediyl] also known as PCDTBT, etc., small organic semiconducting molecules, or inorganic semiconductors such as silicon, Cadmium Telluride, Cadmium Zinc Telluride, etc., or compound semiconductors such as Gallium Nitride, Gallium Indium Arsenide, or liquid state semiconducting materials, or any other material (solid, liquid or gas) that can sense products of interaction between C1 and incident subatomic particles, including neutrons.

In one embodiment, C1 390 may also comprise multiple layers of materials that interact with different subatomic particles, including neutrons of different energies or other subatomic particles like gamma rays, or it may be a composite of various materials, each of which interacts with a different subatomic particle, or it may be a combination of the two approaches.

Further, the presence of C1 390 does not preclude the possibility of incident subatomic particles, including neutrons, interacting directly with materials comprising the sensors. For example, in one embodiment, there may be instances where the materials forming the sensor pixel array are themselves sensitive to the incident subatomic particles, such as silicon is sensitive to gamma rays, muons, etc. or Boron used for p-type doping of silicon is sensitive to neutrons. Further, by way of example, a semiconductor such as silicon may be doped with high neutron capture cross section material such as 157Gd. Also, a semiconductor such as PCBM (fullerene derivative [6,6]-phenyl-C61-butyric acid methyl ester) may be modified chemically with neutron capture materials to render the molecules neutron-sensitive.

In one embodiment, the particle detection system may not include a converter layer C1 390 at all. Instead, converter material that would otherwise be used to create the C1 layer 390 is homogeneously intermixed with the sensor material used to create pixel array, P1 315. By way of example, compounds of neutron capturing material may be intermixed with sensor materials such as semiconducting polymers, e.g., P3HT, PCDTBT, etc., small organic semiconducting molecules, or inorganic semiconductors such as Silicon, CdTe, etc. or compound semiconductors such as Gallium Nitride, Gallium Indium Arsenide, or liquid state semiconducting materials. Further, P1 315 may comprise a pixilated or uniform sensory array made from semiconducting materials or materials sensitive to the products of the interaction between incident subatomic particles and the reactive materials. Also it may comprise composite materials sensitive to subatomic particles and capable of generating a readable signal.

Dispersing the converter material within the sensor material, however, may require printing technology. Also, special processes would be required to intermix the converter material with the sensor. As discussed above, control electronics module 310 can be used for controlling the operation of the element and transmitting any analog or digital signal generated by the element to the remainder of the system.

In one embodiment, each of the elements E1 320 through En 325, may comprise a lensing apparatus L1 305 for focusing the particles towards the sensor with the intent of improving the instrument's sensitivity. For example, if the particle detection system is set up for detecting neutrons, the neutrons can be lensed using appropriate materials such as glass poly-capillary fibers made from lead-silica glass and used for focusing ultra-cold to fast neutrons. Alternatively, if the particle detection system is set up for detecting X-rays, the X-rays can be lensed using appropriate materials such as microstructured capillary arrays.

The array of elements E1 320 through En 325, in one embodiment, is connected, in serial or parallel configuration, to a slave processing unit 335 (referred to herein as "SPU"). In one embodiment, the slave processing unit 335 can be a Field Programmable Gate Array ("FPGA"), a Complex Programmable Logic Device ("CPLD"), a microcontroller, etc. The slave processing unit may also be placed within the elements (internalized) labeled E1 to En thereby minimizing or altogether obviating the need for an external processing unit such as 335. The elements in conjunction with the SPU form a "sensor module" 330.

One or more sensor modules may be placed in a configuration that is optimized to maximize system performance. For example, multiple sensor modules could be configured to operate in parallel so as to increase the sensitivity of the device. Because each of the elements may only be modestly sensitive in detecting incident particles, the overall sensitivity to the particles being detected can be increased by stacking more than one sensor module 330 in parallel.

Each element may be only modestly sensitive in detecting incident particles, but when several of these elements are aggregated in an appropriate architecture, these components act in a concerted fashion to result in a highly sensitive, agile and reliable particle detection instrument. The aggregation of sensors operating in parallel results in higher sensitivity to the particles and resultant imaging as compared to individual elements or an individual module. In one embodiment, the multiple sensor modules can be loaded onto and operate in parallel on a common printed circuit board. In a further embodiment, multiple printed circuit boards, each with at least one sensor module, can be configured to operate and detect particles in parallel to further increase the sensitivity and fidelity of the platform. In one embodiment the multiple sensor modules can all be configured to detect neutrons making the device highly sensitized to neutrons and, accordingly, a highly reliable neutron detection instrument.

Each of the modules can be comprised of multiple elements. In one embodiment, the elements, E1 320 to En 325, can be made as large or small as needed in order, for example, to embed them in confined geometries such as inside the human body for medical applications such as single-photon emission computed tomography ("SPECT"), positron emission tomography ("PET"), etc.

In one embodiment, a subset of the elements E1 320 to En 325 can be configured to detect different particles from the remaining elements by coating them with a different C1 converter layer from the other elements. Accordingly, a single module 330 can be used to detect more than one type of subatomic particle.

Each sensor module 330 is connected to, either wirelessly or through wires, to a system level master processing unit 345 (referred to herein as "MPU") that controls the operation of the SPU on the module and processes the data it receives from the SPU. In one embodiment, the SPU in one of the modules may also be able to serve as the MPU. An MPU, in one embodiment, may be connected to several sensor modules, wherein each sensor module is configured to be sensitive to and detect a different subatomic particle. Alternatively, an MPU may be connected to several stacked sensor modules acting in concert to detect the same particle, e.g., neutrons.

In one embodiment, the MPU 345 may be part of a computing system similar to computing system 110 from FIG. 1 described above in detail. Further, the MPU 345 may also comprise a system memory 116 and storage memory 132 and 133 for storing data received from the various sensor modules similar to computing system 110 in FIG. 1. The MPU 345 may send processed data to the display 350 that has a user interface (UI) that can be used to program the entire system. The display may perform a similar function to display device 124 discussed above in relation to FIG. 1.

Further, the data from the MPU may also be relayed wirelessly through wireless module 380 to a host server 370, wherein the host server may perform a similar function to servers 240 and 245 described in relation to FIG. 2. Each of the client devices 210, 220 and 230 in FIG. 2, in fact, may be a discrete computing system comprising a MPU, connected to its own set of SPUs, and reporting the results of a particle detection operation to a host server 240 or 245 through network 250. For example, client devices 210, 220 and 230 may be security devices installed at an airport to screen passengers' baggage for explosive devices. Each of the client devices could then, in turn, report the results of the screening to a centrally located server 240 or 245. The results from all the various screening operations could also be stored in storage devices 260(1)-(L), storage devices 270(1)-(N), storage devices 290(1)-(M), or intelligent storage array 295. In another embodiment, MPU 345 may relay data to host server 370 through a wired connection (not shown) instead of through wireless module 380.

In one embodiment, the data from the various SPUs could simply flow through an MPU and be transmitted to a host machine 360. The host machine, in one embodiment, could be a personal computer or a tablet PC or even a smart phone that may be a computing system similar to computing system 110 from FIG. 1 described above in detail. The host machine in such an embodiment would be connected to the MPU 345 through a communication interface similar to interface 122 described in detail above.

In this embodiment, the host machine 360 would be responsible for processing the data received from the various SPUs instead of the MPU. The MPU would, however, be responsible for controlling the operation of the various SPUs connected to it. The host machine would therefore perform a similar function to computing system 110. The display 350 may then be connected to the host machine 360, wherein a user of the system could program the system using the display connected to the host machine. Alternatively, in one embodiment, the MPU 345 may reside on host machine 360 instead of within the housing 340 of the particle detection system and control the various SPUs from within the host machine 360.

In one embodiment, the particle detection system of FIG. 3 is encapsulated for protection from the element such as temperature, humidity, dust, etc., by placing it inside a housing 340 made from materials such as plastic, metal, etc. The housing 340, in one embodiment, may be designed to restrict the entry of certain subatomic particles, such as photons in the visible range, ultraviolet range, or more energetic photons such as X-rays or gamma rays, etc. For certain applications, such as neutron detection, for example, the housing 340 may contain materials such as high-density polyethylene ("HDPE") that moderate the incident neutron velocity. The design of the housing 340 and the materials used to construct it will vary depending on the application for the particle detection system. For example, if the detector is being used for oil and gas exploration within oceanic waters, the housing 340 will need to be constructed with materials able to withstand extremely high subterranean temperature and pressure.

Figure 4:
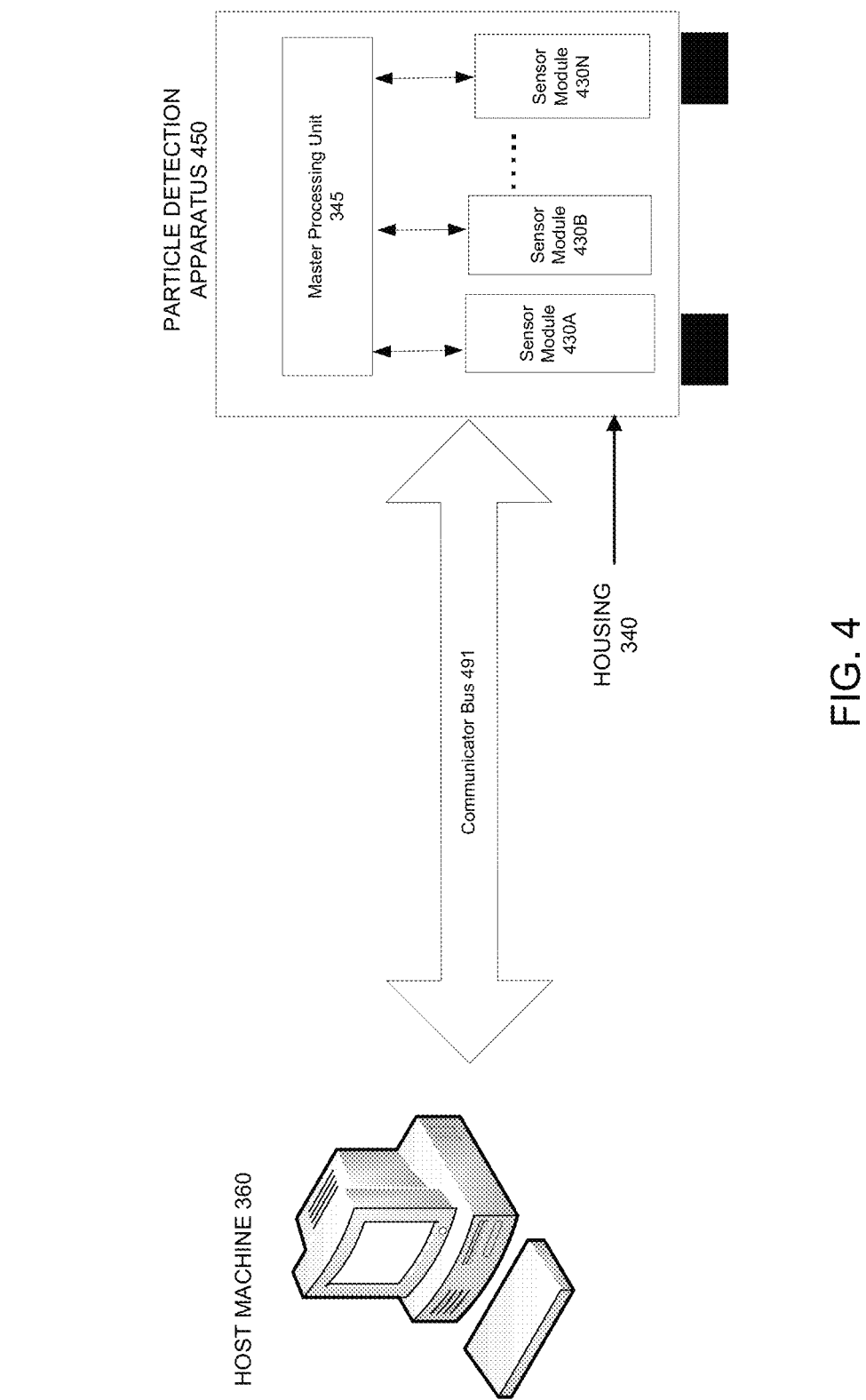
FIG. 4 is a schematic block diagram illustrating a typical hardware configuration for connecting the host machine with the sensor modules in accordance with one embodiment of the present invention.

FIG. 4 is a schematic block diagram illustrating a typical hardware configuration for connecting the host machine with the sensor modules. The embodiment illustrated in FIG. 4 is one wherein the display 340 and UI is connected to or implemented within host machine 360 as described above. The host machine 360 is responsible for processing the data it receives from MPU 345 over communicator bus 491. MPU 345 is responsible for controlling the operation of the various SPUs on sensor modules 430A-430N. Sensor modules 430A-430N perform essentially the same function as sensor module 330 from FIG. 3. Each of the sensor modules 430A-430N shown in FIG. 4 may be configured to detect a different subatomic particle. Alternatively, as discussed above, the sensor modules 430A-430N may be stacked and operating in parallel to reliably detect the same particle, e.g., neutrons. By using a plurality of sensor modules acting in concert, the sensitivity and reliability of the system can be vastly improved.

The sensor modules 430A-430N constitute a module array that can plug directly into board sockets within the particle detection chassis 450. The MPU 345 may be populated on the same board that comprises the sockets for plugging in sensor modules 430A-430N, or one of the SPU's in 430A to 430N may be programmed to serve the function of MPU 345, thereby eliminating the need for a separate MPU 345. Because they plug into board sockets, the sensor modules can be easily inserted and removed from apparatus 450. Further, the placement of the sensor modules 430A-430N can be determined based on the type of particle each sensor module is configured to detect and how sensitive to the particle the user needs the system to be.

Host machine 360 uses communication interface 122, as illustrated in FIG. 1, to communicate with the particle detection apparatus 450 encapsulated within housing 340 over communicator bus 491. The communicator bus 491 provides a high-speed electronic communication channel between the host machine 360 and the particle detection apparatus 450. The communicator bus can also be referred to as a backplane, a module connection enabler, or system bus. Physically, communicator bus 491 is a fast, high-bandwidth duplex connection bus that can be electrical, optical, etc.

Particle detection apparatus 450 can, in one embodiment, also be used in a standalone mode, such as a handheld instrument, backpack instrument etc. In this embodiment, the housing of the apparatus 450 would comprise MPU 345, the display 350, a wireless module 380, and one or more sensor modules 330, so that the user could freely use the particle detector without needing to physically connect to a host machine. The particle detection apparatus 450 can, in another embodiment, be also connected through a wired (such as Ethernet or USB) or wireless (Bluetooth, Wi-Fi) to a computing device such as tablet PC or smart phone. In this embodiment, there will be no need for a display 350 on the detection apparatus. As discussed above, MPU 345 could be part of a computing system similar to computing system 110 illustrated in FIG. 1 with an associated memory and display. Such a system, along with its modules, could serve as a component in an assembly of systems that would be placed at desired locations arbitrarily far from each other to act as agents for detecting subatomic particles over large geographic regions, on land, underground, on water, underwater, or any other location including space. Data gathered from the various agents may be relayed to a central host machine 370 and analyzed to prepare maps of incident particles across any geographic region.

In one embodiment, the module 330 can be programmed to determine the rate of subatomic particles incident on it. Alternatively, the MPU can be programmed to collect information from the SPUs connected to it and determine the rate of various subatomic particles incident on the entire apparatus 450. In another embodiment, particle detection apparatus 450 can be configured to establish the direction of incident particles by placing the modules 430A-430N within it in an appropriate geometric configuration, e.g., around a sphere, or in a stacked parallel configuration. For example, the direction of neutrons can be determined by using a neutron absorbing collimator or neutron absorbing grid of apertures in front of the detector apparatus that will block all neutrons incident on them and will allow the passage of incident neutrons through windows in the grid or collimator.

In yet another embodiment, appropriate design of material used to develop sensor pixel P1 315, such as fully depleted deep CMOS or CCD sensors made from inorganic or organic semiconductors, will allow the system to determine the energy of incident subatomic particles including neutrons and thereby enable spectroscopy.

Further, in one embodiment, the entire system, or each module in the system, or even each element in the system can be tuned to be sensitive to different subatomic particles. For example, module 430A can be configured to be more sensitive to gamma rays while module 430B can be configured to be more sensitive to neutrons. Conversely, the modules can also be configured, in one embodiment, to be insensitive to certain subatomic particles. One method to make the modules insensitive to certain subatomic particles is to coat the converter layer C1 with appropriate blocking layers that reduce sensitivity to certain particles. This chemical tenability is an advantageous feature of the present invention because it gives a user the unique flexibility to configure a system to be sensitive to a select subset of subatomic particles of interest while being insensitive to other particles that the user may not be interested in tracking.

Figure 5A:
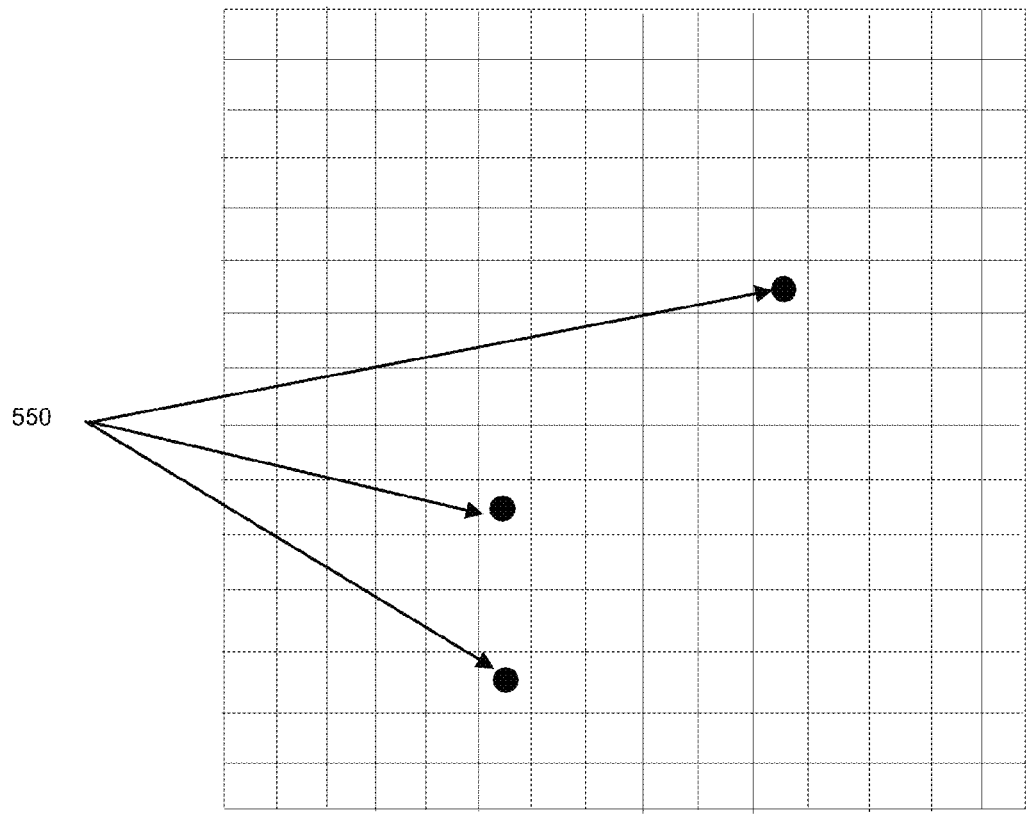
FIG. 5A is an exemplary block diagram of a sensor array of pixels in accordance with one embodiment of the present invention.

In one embodiment, choosing elements E1 320-En 325 that are highly pixelated can significantly increase the granularity of the particle detection device. For example, the more pixels an element can comprise, the easier it is for the system to detect the location and direction a particular particle came from. It also makes it easier to detect the particle's energy. FIG. 5A is an exemplary block diagram of a sensor array of pixels in accordance with one embodiment of the present invention. As seen in FIG. 5A, the higher the number of pixels on pixel array P1 315, the more granular it is and the easier it is to precisely detect the position of particles 550.

Figure 5B:
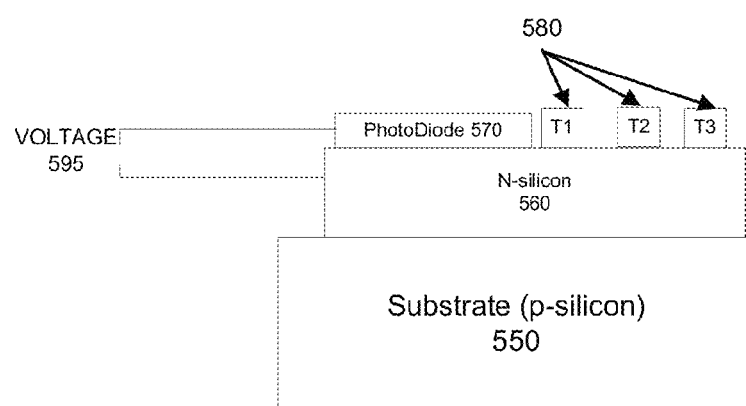
FIG. 5B is an exemplary block diagram illustrating the cross-sectional view for each pixel in accordance with one embodiment of the present invention.

FIG. 5B is an exemplary block diagram illustrating the cross-sectional view for each pixel on the sensor array of pixels in accordance with one embodiment of the present invention. As discussed above, the sensor may be an off-the-shelf component typically found in a conventional digital camera The electronics for the pixel may be mounted on silicon substrate, comprised of p-silicon 550 and n-silicon 560. The area of the pixel that collects information regarding incident particles, e.g., photons is photo-diode 570. The pixel may also comprise three transistors 580, T1, T2 and T3, that are used to collect the information captured by the photodiode. For example, if subatomic particles or products of the reaction between the incident subatomic particle and the converter layer (390 in FIG. 3) impinge upon photo-diode 570, voltage (or current) 595 is induced through a combination of distortion and ionization of the electron field within the photodiode as well as the photoelectric effect. The energy of individual incident subatomic particles or products of the reaction between a single incident subatomic particle and the converter layer (390 in FIG. 3) impinging on photo-diode 570 dictates how much charge accumulates within the pixels. If several particles become incident during the time when the sensor is in an exposed state, a proportionately larger number of islands of pixels will accumulate charge. The transistors are used to collect information regarding the accumulated charge during a capture cycle and convey this information to an A/D converter within control electronics module 310. Each pixel may report an A/D converted value of between 0 and 1024 based on the intensity of impingement on the pixel.

In certain embodiments, C1 390 may be reactive to more than one type of subatomic particle. For example, materials that react with neutrons may also react with high energy gamma rays. In another example, the converter materials may interact only with neutrons but the sensor materials may interact with a host of other sub-atomic particles including gamma photons, alpha particles, fast electrons etc. In these embodiments, a discrimination process may be run on MPU 345 that is used to discriminate between the different types of particles while minimizing any false positives. Each subatomic particle may be unique with respect to the intensity values they generate or the pattern in which they impinge on the pixels of pixel array P1 315. The discrimination procedure comprises information regarding all the particles' unique "signatures" and uses these to differentiate between particles to ensure that false positives are not generated.

For example, incident neutrons particles interact with the material in C1 or the material of the sensor pixels and produce one type of electric signal and gamma rays produce another type of signal or pattern of islands of pixels in which charge is generated beyond the thermally generated charges. Hence, discriminating between neutrons and non-neutrons becomes much faster and simpler than in proportional tubes or scintillator detection systems that must collect a significant amount of statistical information in order to implement the pulse shape discrimination algorithms for particle discrimination. The proposed system is capable of detecting single neutrons and being able to distinguish them from single non-neutron particles, such as gamma photons.

This ability to discriminate between single neutron and non-neutron particles is enabled by unique digital signatures for each type of particle. The term digital signature here refers to patterns of islands of pixels where charge gets deposited by the incident particles or products of the interaction between the incident particles and the converter layer C1. Therefore, not only can a neutron be distinguished from other non-neutron particles, but also the non-neutron particles can be further distinguished as gamma photons, x-ray photons, alpha particles, fast electrons etc. Furthermore, every radioactive material (or radionuclide) emits a unique family of sub-atomic particles. For example, highly enriched uranium emits neutrons and gamma photons. Since at least some or all of these subatomic particles are detected and discriminated in the proposed system with the help of its discriminating procedure, the source (radionuclide/isotope etc.) of these particles can be identified by referring to a library of digital signatures in the system's memory or a memory external to the system.

One application of the novel discrimination procedure of the present invention is in the oil and gas exploration industry. A drill used for oil exploration, for example, could comprise both a source of neutrons and the particle detection system of the present invention. Further, the drill can comprise a source of gamma radiation as well. Both gamma and neutron data collected with the help of the novel discrimination procedure provide vital information regarding the porosity and lithology of rock formations.

Another application of the novel discrimination procedure would be in the homeland security industry. For example, airport security scanners may employ the particle detection system of the present invention to detect SNMs. However, because certain individuals carry radioactivity in their body, they may radiate high energy gamma rays that would result in a false alarm being generated by the scanner if not for the particle discrimination procedure of the present invention. As discussed above, certain materials chosen for C1 may react with both neutrons and high energy gamma rays. Using the unique "digital" signature for the neutrons, gamma rays, and other particles, the discrimination procedure of the present invention prevents the generation of false positives. The unique digital signatures also enable identification and counting of gamma photons, as well as the identification of the source from which the neutrons and other particles originated. One example of this capability is that the discrimination procedure can distinguish between a weapons grade Plutonium source and a non-neutron (and dominantly gamma emitting) source such as $^{137}$Cs or $^{60}$Co or $^{133}$Ba.

Figure 6A:
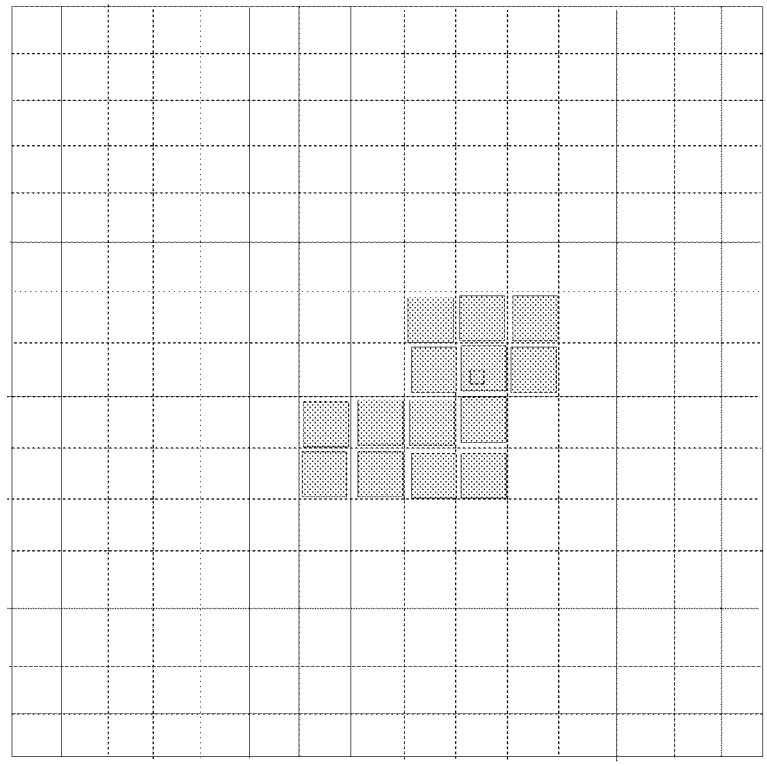
FIGS. 6A and 6B illustrate two exemplary patterns created by two different types of subatomic particles and as detected by a pixel array of sensors in accordance with one embodiment of the invention.
Figure 6B:
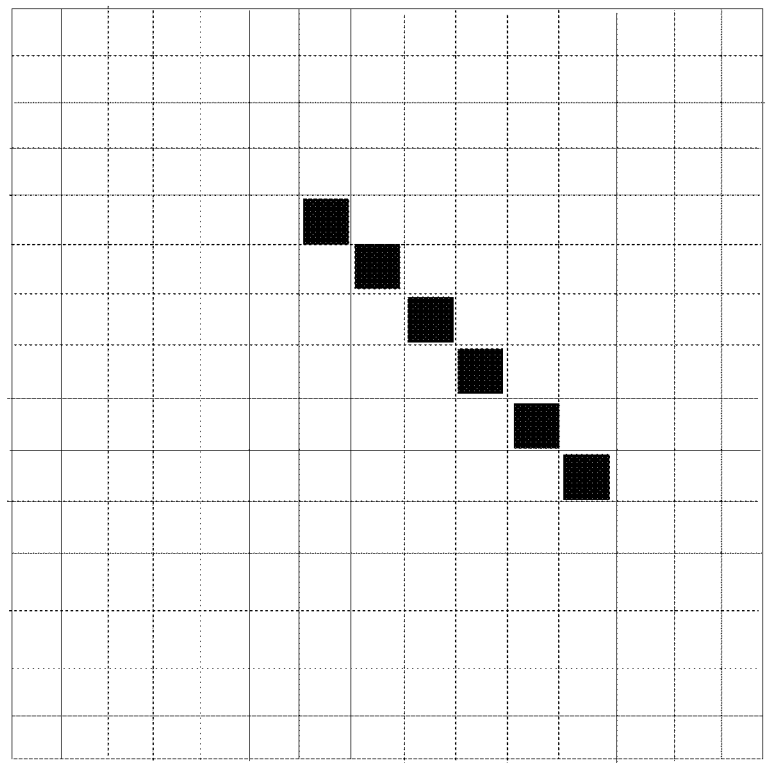

FIGS. 6A and 6B illustrate two exemplary patterns created by two different types of subatomic particles and as detected by a pixel array of sensors in accordance with one embodiment of the invention. FIG. 6A illustrates a pattern created by hypothetical Particle A, while FIG. 6B illustrates a pattern created by hypothetical Particle B. If both Particle A and Particle B are detected by the same sensor P1 315 because converter layer C1 390 reacts with both types of particles, or the converter layer C1 390 interacts with Particle A and the sensor material interacts with Particle B, then a discrimination procedure is required to be able to tell the particles apart so as not to generate false positives. The discrimination procedure will be programmed to recognize that Particle A will create a pattern of islands of pixels of intensity statistically different from Particle B, and further that the pattern will comprise of pixels that are clumped together as opposed to the diagonal or other types of pattern generated by Particle B. Accordingly, the discrimination procedure can use the respective signatures of Particle A and Particle B to distinguish between each other.

The discrimination procedure can, in one embodiment, compare a pattern created by a particle to a library patterns stored in memory 116 of host machine 360 to identify which of the patterns in memory the particle most closely resembles in order to identify the particle.

It is important to note that in one embodiment of the present invention the signature patterns of various different particles can be identified at the same time. For example, the discrimination procedure would be configured to identify both Particle A and Particle B at the same time in the example illustrated in FIGS. 6A and 6B. Further, if other particles were detected in the system, those particles could be identified using their digital signatures at the same time as well.

Figure 9:
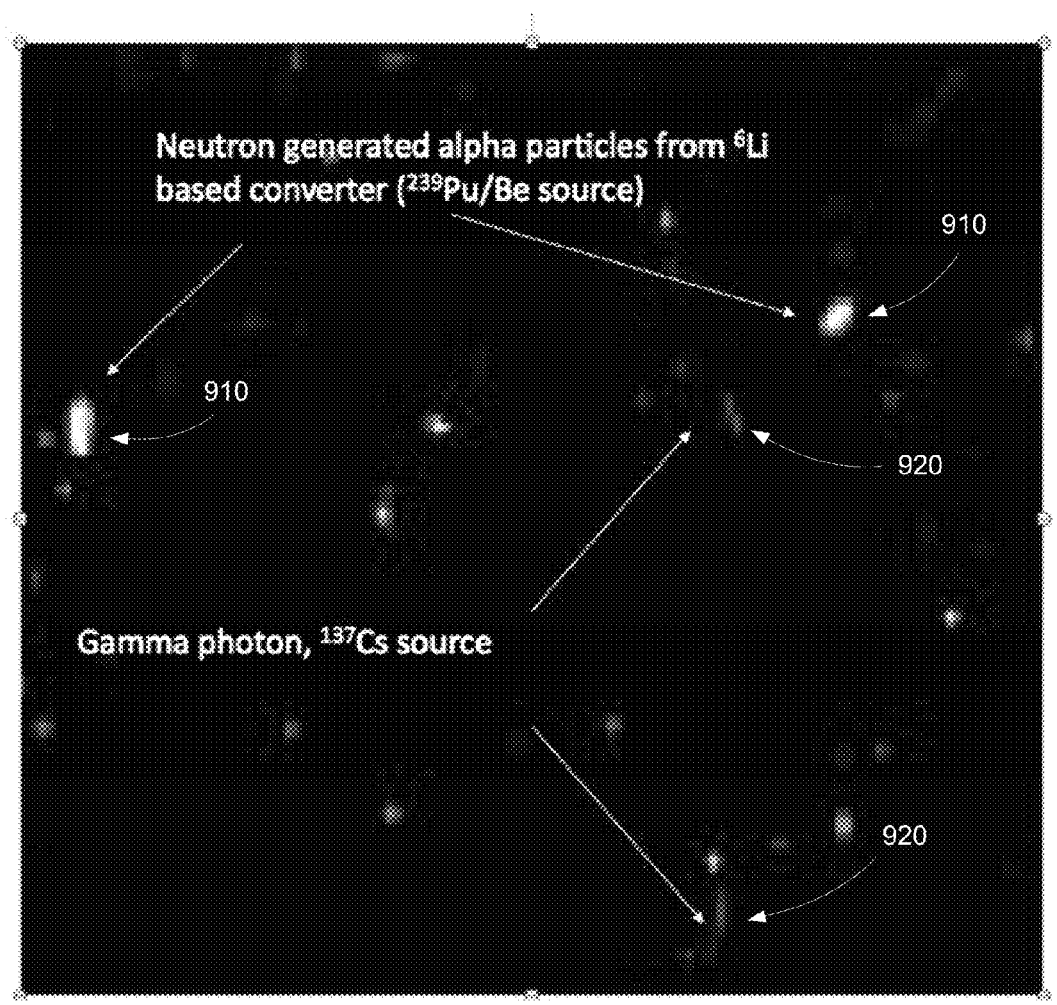
FIG. 9 illustrates exemplary signatures for neutron and gamma particles used to distinguish between the two particles in accordance with one embodiment of the present invention.

FIG. 9 illustrates exemplary signatures for neutron and gamma particles used to distinguish between the two particles in accordance with one embodiment of the present invention. The discrimination procedure discussed above can be configured to detect pattern 910 associated with neutron generated alpha particles and distinguish pattern 910 from pattern 920 associated with gamma photons. Thus, discrimination procedure can identify both neutrons and gamma photons and distinguish them from each other.

In one embodiment, the digital signature can be generated using several stacked sensor modules, e.g., 430A-430N in FIG. 4. In this embodiment, the generated digital signature can be a vector in three dimensional space. The discrimination procedure uses information, e.g., coordinates of sensors, intensity of impingement based on the A/D read-out from the pixels, time of impingement etc. to determine a pattern of impingement in three dimensional space and compares the pattern to the digital signatures stored in memory and performs a statistical match in order to determine the identity of the particle. Performing digital signature comparison in three dimensional space allows for increased reliability in the system. For example, certain particles with higher energy may leave a pattern of higher intensity on the surface modules as opposed to modules deeper within the stack. Or, for example, particles such as neutrons and gamma photons with higher momentum may leave a pattern of higher intensity on modules deeper within the stack but only a trail of lower intensity on the surface modules. Thus, analyzing the intensity of the reaction of the particles with the sensors at different layers of the module stack allows for increased fidelity and accuracy.

Furthermore, in one embodiment of the present invention the noise generated and accumulated within the pixels due to thermal or any other reason, and especially during the time interval of exposure, can be eliminated. The methods for reducing or completely eliminating such noise may include: (a) timely resetting of individual pixels or aggregates of pixels or entire rows and columns of pixels within the pixels; (b) optimization of exposure, readout and reset time cycles so that pixels are reset as often as is required; (c) changing the temperature of operation of the sensors, such as cooling them down.

In one embodiment, the discrimination procedure may use patterns created by charge building up in the pixels of the underlying sensor. For example, the neutrons may interact with the converter layer and undergo a nuclear reaction. For example, if the converter material contains $^{157}$Gadolinium, the reaction will be $^{157}$Gd+n=$^{158}$Gd*=>$^{158}$Gd+gamma+x-rays+IC e−+ACK e−. In one embodiment, the products of this reaction will enter the sensor and create a build up of charge in the pixel that they interact with first. The high energy of these reaction products will cause secondary ionization within the pixel that will lead to enhanced charge build-up within the pixel. Furthermore, the high kinetic energy of these reaction products will also cause them to scatter on to neighboring pixels and a track of built-up charges will be left within the sensor. The discrimination procedure within the instrument examines these tracks and determines the form of the particle. Hence, if the discrimination procedure in the processing unit of the instrument (or module) determines that a gamma-ray and/or an x-ray and/or an IC electron and/or an ACK electron were found in the sensor, it will be concluded that a neutron interacted with the converter layer and the neutron count tracked by the MPU is incremented by one.

Similarly, by way of another example, if the converter layer contains $^{10}$Boron and the incident neutron interacts with $^{10}$Boron, the following reaction will follow: $^{10}$B+n->$^7$Li+Alpha. These reaction products will travel in nearly mutually opposite direction and one of them will interact with the sensor, thereby leaving a unique build-up of charge. For instance, alpha particles have a very high rate of loss of energy within semiconductors and solids in general. Consequently, the build-up of charge in pixels is found to be uniquely concentrated to a few pixels only. The discrimination procedure within the processing unit is able to interpret the "signature" of alpha particles (or $^7$Li) uniquely and discriminate this signature against any other radiation that might be incident on the instrument, such as gamma rays. As a result, the instrument is able to discriminate neutrons from any other sub-atomic particle.

The present invention is highly scalable because not only does it use relatively cost effective off-the-shelf components that may be chemically tuned using appropriate converter layers or converter materials blended with sensor materials, but also users have the ability to incorporate as many sensor modules within an apparatus as needed. Further, because the parts of the present invention are readily available and low cost, they are relatively easy to replace. Accordingly, if a sensor module gets damaged, it will typically be less troublesome to replace it than to fix it.

Further, another advantage of the present invention is that the housing 340 of the particle detection system is flexible and can be configured in ways specifically customized for several different applications. For example, the housing may be chosen in a way so that the pixel arrays can be stacked or tiled side by side along a wall of a cargo container, and used to detect radiation in containers being shipped. In particular, for example, in the case of neutron detection, there is great flexibility in how the pixel arrays are arranged because, with some very limited exceptions, neutrons can penetrate most matter until they make contact with a material that they interact with. Also, as discussed above, particle detection apparatus 450 can be configured to establish the direction of incident particles by placing the modules 430A-430N within it in an appropriate geometric configuration, such as around a sphere. In this case, the housing 340 would be spherical. Alternatively, in other embodiments, the system can be designed to fit in a hand held device or a backpack device.

In yet other embodiments, the modules 330 and any other printed circuit boards ("PCBs") within the housing 340 may be constructed using flexible materials, so that the system can be imbedded in clothing and other areas where using rigid materials would not be pragmatic. Further, using flexible materials allows the surface area of the detector to increase, thereby, increasing the sensitivity of the system. This advantageously allows the present invention to be utilized for various different applications using the same system design.

In one embodiment, the MPU 345 processes the data from the various SPUs it is connected to and performs all the calculations necessary to determine if a particular particle has been detected. The MPU 345 can use the information from the pixel arrays of the elements E1 320 through En 325 to determine precisely the coordinates of the pixels that tested positive for the particle. The MPU 345 may create a vector of information for each pixel comprising the coordinate of the pixel and the element and sensor module it is located within.

Figure 7:
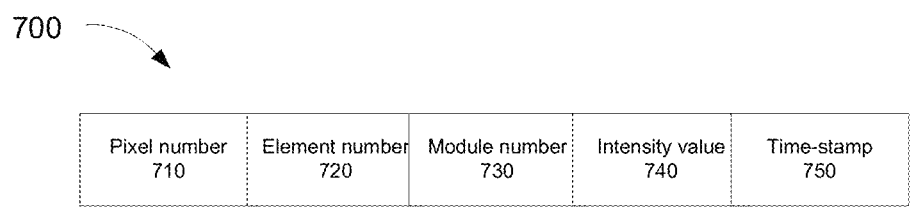
FIG. 7 illustrates an exemplary information vector created for each pixel by the MPU in accordance with one embodiment of the present invention.

FIG. 7 illustrates an exemplary information vector created for each pixel by the MPU in accordance with one embodiment of the present invention. The information vector 700 may comprise information regarding the pixel number or (x,y) coordinate 710, information regarding the element or sensor number 720, and information regarding module number 730 on which pixel 710 and element 720 reside. Also, the vector may comprise information regarding the intensity value 740 read out from the pixel and a timestamp 750. This vector of information can either be stored in memory for further analysis or passed on to display 350 for a user to visually analyze the data or passed along to a computing device (such as a tablet PC or smart phone) attached to the detector box through a wired or wireless connection. Alternatively, the information may be relayed to a remote location through wireless module 380. The MPU 345 may also compare the vectors received from a pixel array to the various signatures of different subatomic particles stored in memory to determine or confirm the identity of the particle.

Further, the MPU 345 can be programmed to flag an alarm for the user of the system if more than a critical threshold number of particles are detected over a certain period of time and over a certain area. For example, in one embodiment, when the detection instrument is rendered as a handheld instrument homeland security applications, the MPU 345 may be programmed to flag an alarm on the display 350 if more neutrons are detected per unit volume of the instrument than the background.

Figure 8:
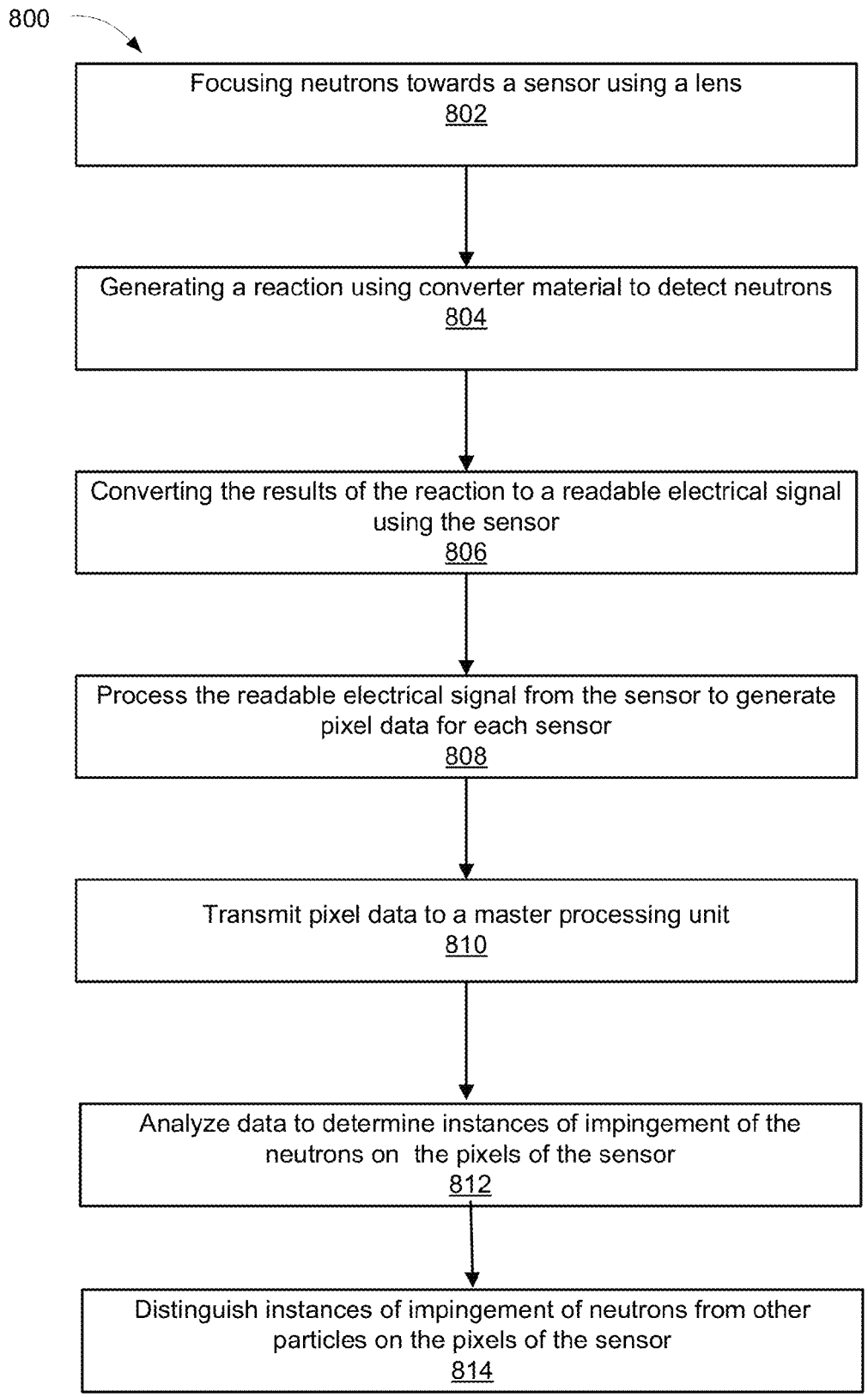
FIG. 8 depicts a flowchart 800 of an exemplary process of detecting subatomic particles, according to an embodiment of the present invention.

FIG. 8 depicts a flowchart 800 of an exemplary computer controlled process of detecting subatomic particles, according to an embodiment of the present invention. The invention, however, is not limited to the description provided by flowchart 800. Rather, it will be apparent to persons skilled in the relevant art(s) from the teachings provided herein that other functional flows are within the scope and spirit of the present invention. Flowchart 800 will be described with continued reference to exemplary embodiments described above, though the method is not limited to those embodiments.

At step 802, neutrons, or other subatomic particles, may be lensed towards a sensor E1 320 by using a lensing apparatus L1 305. Focusing the neutrons towards the sensor improves the instrument's sensitivity as discussed above.

At step 804, a reaction is generated when the neutrons, or other subatomic particles, come into contact with converter layer, C1 390. The converter layer can interact with the incident neutrons to generate a reaction, the results of which are then converted by a sensor array of pixels, P1 315, to a readable electrical signal at step 806 using control electronics module 310. As discussed above, in one embodiment, converter layer C1 may comprise multiple layers of materials that interact with different subatomic particles, including neutrons, or it may be a composite of materials, each of which interact with a different subatomic particle. Further, in one embodiment, instead of being a discrete layer, the C1 layer may be intermixed with the sensory array P1 315 itself.

At step 808, SPU 335 processes the signal from the various elements, E1 320 to En 325, to generate pixel data for each sensor. While each element E1 320 to En 325 individually may have modest sensitivity for detecting the incident subatomic particles, the elements in aggregate result in a highly sensitive level of detection.

At step 810, the pixel data is transmitted to MPU 345. The MPU 345 controls the various SPUs connected to it, collects the data from the SPUs, and analyzes the data at step 812 to determine the impingement of any neutrons on the pixels of sensor 315. At step 814, the MPU 345 runs the discrimination procedure used to discriminate between the different types of particles without generating any false positives. For example, the MPU 345 may be programmed to discriminate neutrons from other particles such as high energy gamma rays may be coincident with the neutrons.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered as examples because many other architectures can be implemented to achieve the same functionality.

The process parameters and sequence of steps described and/or illustrated herein are given by way of example only. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. These software modules may configure a computing system to perform one or more of the example embodiments disclosed herein. One or more of the software modules disclosed herein may be implemented in a cloud computing environment. Cloud computing environments may provide various services and applications via the Internet. These cloud-based services (e.g., software as a service, platform as a service, infrastructure as a service, etc.) may be accessible through a Web browser or other remote interface. Various functions described herein may be provided through a remote desktop environment or any other cloud-based computing environment.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

Embodiments according to the invention are thus described. While the present disclosure has been described in particular embodiments, it should be appreciated that the invention should not be construed as limited by such embodiments, but rather construed according to the below claims.

What is claimed is:

1. A method of detecting particles, said method comprising:
    generating a reaction to a plurality of particles using a plurality of different converter materials, wherein each of said converter materials are designed to generate a detectable reaction with one of said plurality of particles;
    converting a response to said reaction to a readable electrical signal using a plurality of discrete pixel sensor arrays wherein each pixel sensor array is composed of one of the plurality of different converter materials such that each pixel sensor array is designed to detect a different type of particle in said plurality of particles;
    processing said readable electrical signal from said plurality of pixel sensor arrays to generate information regarding each pixel on said pixel sensor arrays;
    transmitting said information to a processing unit; and
    analyzing said information using said processing unit to determine instances of impingement of said plurality of particles on each of said pixel sensor arrays;
    wherein each pixel sensor array is in communication with a particle discrimination algorithm dedicated to detecting a type of particle in said plurality of particles that the converter material included in the pixel sensor array is designed to detect, and
    wherein each discrimination algorithm distinguishes between instances of impingement of a type of particle it is dedicated to detect and impingement of particles it is not dedicated to detect.

2. The method of claim 1, wherein said pixel sensor arrays are readily available sensors used in consumer electronic device camera systems.

3. The method of claim 1, further comprising focusing said plurality of particles towards said pixel sensor arrays using a lens apparatus.

4. The method of claim 1, wherein said analyzing further comprises creating an information vector for each pixel on each pixel sensor array, wherein information for said information vector is selected from a group consisting of:
    a location value for a pixel;
    an intensity value for said pixel, wherein said intensity value is a measure of intensity related to an impingement of at least one particle on said pixel; and
    a time-stamp for said pixel, wherein said time-stamp records the time at which said impingement occurred.

5. The method of claim 1, wherein said plurality of particles is selected from a group of subatomic particles consisting of: neutrons, gamma rays, beta particles, alpha particles, neutrinos, and ions.

6. The method of claim 1, wherein said plurality of particles is selected from a group consisting of: subatomic particles, atoms and molecules.

7. The method of claim 1, further comprising: increasing sensitivity to said plurality of particles by using a plurality of said pixel sensor arrays, wherein said plurality of said pixel sensor arrays are configured to operate in parallel.

8. The method of claim 7, further comprising: determining a pattern of impingement of said plurality of particles on said plurality of said pixel sensor arrays; and
    displaying said pattern of impingement on a display screen of a graphical user interface.

9. The method of claim 8, wherein said plurality of said pixel sensor arrays are loaded on a plurality of printed circuit boards, wherein said plurality of printed circuit boards are configured to detect said plurality of particles in parallel, and further wherein each of said plurality of printed circuit boards comprises at least one of said pixel sensor arrays.

10. The method of claim 8, further comprising:
    determining a pattern of impingement of said plurality of particles on said plurality of said pixel sensor arrays in three dimensional space; and
    comparing said pattern of impingement to a library of digital particle signatures to determine a respective identity of said plurality of particles.

11. The method of claim 8, wherein a source of said plurality of particles is determined based on said pattern of impingement, wherein said source is selected from a group consisting of: radionuclide and non-radionuclide.

12. The method of claim 1, further comprising: eliminating noise generated within said pixel sensor arrays.

13. An apparatus for detecting particles, said apparatus comprising:
    a plurality of different converter materials operable to generate a reaction to a plurality of particles, wherein each of said converter materials are designed to generate a detectable reaction with one of said plurality of particles;
    a plurality of pixel sensor arrays operable to convert a response to said detectable reaction to a readable electrical signal, wherein each of said plurality of pixel sensor array is composed of one of the plurality of different converter materials such that each pixel sensor array is designed to detect a different type of particle in said plurality of particles;
    a processing device configured to:
        process said readable electrical signal from said plurality of pixel sensor arrays to generate information regarding each pixel on said pixel sensor arrays;
        analyze said information to determine instances of impingement of said plurality of particles on each of said pixel sensor arrays, wherein each pixel sensor array is in communication with a particle discrimination algorithm dedicated to detecting a type of particle in said plurality of particles that the converter material included in the pixel sensor array is designed to detect; and
    wherein each discrimination algorithm distinguishes between instances of impingement of a type of particle it is dedicated to detect and impingement of particles it is not dedicated to detect.

14. The apparatus of claim 13, further comprising:
a housing operable to encapsulate said plurality of pixel sensor arrays and said processing unit, wherein said housing is designed to restrict entry of certain select particles.

15. The apparatus of claim 14, wherein said housing is constructed using flexible materials.

16. The apparatus of claim 13, further comprising:
a display module for displaying information regarding said instances of impingement through a graphical user interface, wherein said housing further comprises said display module.

17. The apparatus of claim 16, wherein said display module is configured to flag an alarm for a user when said instances of impingement cross over a predetermined threshold value.

18. The apparatus of claim 13, wherein each of said plurality of pixel sensor arrays comprises a plurality of sensor elements, and wherein each of said plurality of sensor elements comprises a lens apparatus, wherein said lens apparatus is configured to focus said plurality of particles towards a respective sensor of an element.

19. The apparatus of claim 13, wherein said plurality of said pixel sensor arrays are loaded on a plurality of printed circuit boards, wherein said plurality of printed circuit boards are configured to detect said plurality of particles in parallel, and further wherein each of said plurality of printed circuit boards comprises at least one of said pixel sensor arrays.

20. The apparatus of claim 19, wherein each of said plurality of printed circuit boards are designed using flexible materials.

21. The apparatus of claim 13, wherein a source of said plurality of particles is determined based on a pattern of impingement, wherein said source is selected from a group consisting of: radionuclide and non-radionuclide.

22. The apparatus of claim 19, wherein each of said plurality of pixel sensor arrays is easily detachable from a respective printed circuit board.

23. The apparatus of claim 22, wherein a pixel sensor array can be detached from a respective printed circuit board and replaced with an easily available pixel sensor array from a consumer electronic device camera.

* * * * *